(12) United States Patent
Boylan et al.

(10) Patent No.: US 6,830,638 B2
(45) Date of Patent: Dec. 14, 2004

(54) MEDICAL DEVICES CONFIGURED FROM DEEP DRAWN NICKEL-TITANIUM ALLOYS AND NICKEL-TITANIUM CLAD ALLOYS AND METHOD OF MAKING THE SAME

(75) Inventors: John F. Boylan, Murrieta, CA (US); William J. Boyle, Fallbrook, CA (US); Kevin M. Magrini, Oceanside, CA (US); Scott J. Huter, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/155,910

(22) Filed: May 24, 2002

(65) Prior Publication Data

US 2003/0217794 A1 Nov. 27, 2003

(51) Int. Cl.⁷ .............................. C22F 1/10; C22K 1/00
(52) U.S. Cl. ...................... 148/563; 148/402; 148/670; 148/676; 623/1.18
(58) Field of Search ................. 148/402, 563, 148/670, 671, 676, 677; 623/1.18, 1.19

(56) References Cited

U.S. PATENT DOCUMENTS

| | | | |
|---|---|---|---|
| 4,665,906 A | | 5/1987 | Jervis |
| 5,067,957 A | | 11/1991 | Jervis |
| 5,190,546 A | | 3/1993 | Jervis |
| 5,230,348 A | * | 7/1993 | Ishibe et al. ................ 604/280 |
| 5,486,183 A | | 1/1996 | Middleman et al. |
| 5,509,923 A | | 4/1996 | Middleman et al. |
| 5,597,378 A | | 1/1997 | Jervis |
| 5,607,444 A | | 3/1997 | Lam |
| 5,611,874 A | * | 3/1997 | Zadno-Azizi et al. ....... 148/402 |
| 5,632,746 A | | 5/1997 | Middleman et al. |
| 5,641,364 A | * | 6/1997 | Golberg et al. ............. 148/563 |
| 5,720,754 A | | 2/1998 | Middleman et al. |
| 5,759,192 A | | 6/1998 | Saunders |
| 5,780,807 A | | 7/1998 | Saunders |
| 5,876,434 A | | 3/1999 | Flomenblit et al. |
| 5,951,793 A | * | 9/1999 | Mitose et al. ............... 148/402 |
| 6,004,629 A | | 12/1999 | Madigan |
| 6,106,642 A | | 8/2000 | DiCarlo et al. |
| 6,131,266 A | | 10/2000 | Saunders |
| 6,165,292 A | * | 12/2000 | Abrams et al. ............. 148/563 |
| 6,508,803 B1 | * | 1/2003 | Horikawa et al. .......... 604/523 |
| 6,602,272 B2 | * | 8/2003 | Boylan et al. .............. 606/200 |

FOREIGN PATENT DOCUMENTS

| | | | |
|---|---|---|---|
| EP | 0873734 A2 | | 10/1998 |
| JP | 2000-140124 | * | 5/2000 |
| WO | 03/028796 A1 | * | 4/2003 |

OTHER PUBLICATIONS

T.W. Duerig, et al., "Linear Superelasticity in Cold Worked Ni Ti," Engineering Aspects of Shape Memory Alloys, pp. 414 19 (1990).

* cited by examiner

Primary Examiner—George Wyszomierski
(74) Attorney, Agent, or Firm—Fulwider Patton Lee & Utecht LLP

(57) ABSTRACT

Nickel-titanium alloys that have been deep drawn in a cold working process have linear pseudoelastic behavior without a phase transformation or onset of stress-induced martensite. A medical device made from a structural element which has been deep drawn and subsequently formed into a desired medical device geometry will experience such linear pseudoelastic behavior.

20 Claims, 6 Drawing Sheets

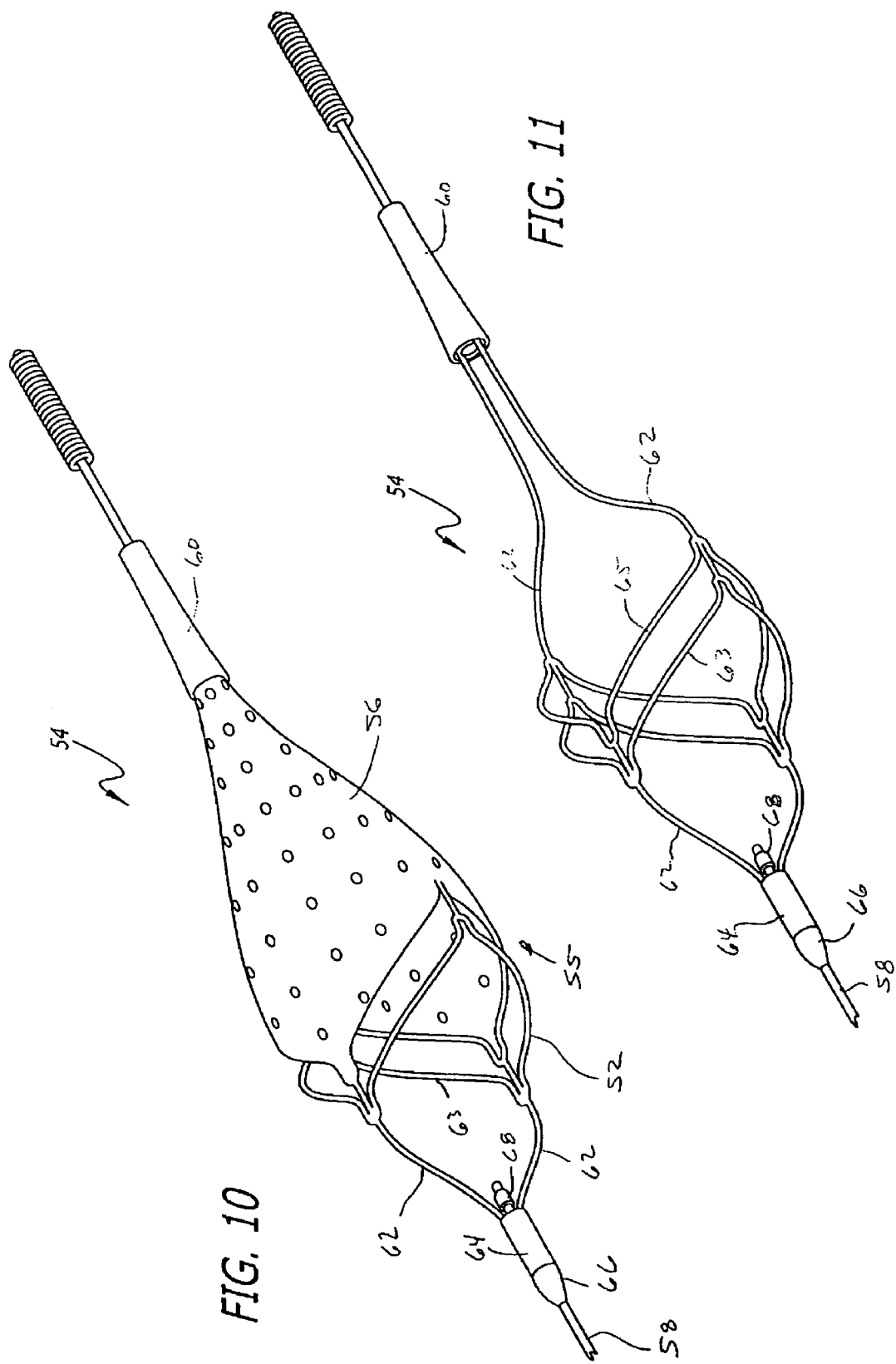

MEDICAL DEVICES CONFIGURED FROM DEEP DRAWN NICKEL-TITANIUM ALLOYS AND NICKEL-TITANIUM CLAD ALLOYS AND METHOD OF MAKING THE SAME

BACKGROUND OF THE INVENTION

The present invention relates generally to application of nickel-titanium alloys to form medical devices. More precisely, the present invention is directed to cold worked nickel-titanium alloys and nickel-titanium clad alloys that have been processed by a deep drawing operation to produce a material exhibiting linear pseudoelastic behavior without a phase transformation or onset of stress-induced martensite that can be manufactured into a medical device.

A focus of developmental work in the treatment of heart disease is an endoprosthetic device referred to as a stent. A stent is a generally cylindrically shaped intravascular device that is implanted in a diseased artery to hold it open. The device is used to maintain the patency of a blood vessel immediately after intravascular treatments, and further reduces the likelihood of restenosis. In some circumstances, a stent can be used as the primary treatment device where it is expanded to dilate a stenosis and then left in place.

A limitation of some prior art stents, especially those of the balloon expandable type, is that they are stiff and inflexible. Often, the expandable type stents are formed from stainless steel alloys and are constructed so that they are expanded beyond their elastic limit. Such stents are permanently deformed beyond their elastic limits in order to hold open a body lumen and to maintain the patency of the body lumen. By the same token, since the material is stressed beyond its elastic limit into the plastic region, the material becomes stiff and inflexible.

There are several commercially available stents that are widely used and generally implanted in the coronary arteries after a PTCA (Percutaneous Transluminal Coronary Angioplasty) procedure, described above. Stents also can be implanted in vessels that are closer to the surface of the body, such as the carotid arteries in the neck or the peripheral arteries and veins in the leg. Because these stents are implanted so close to the surface of the body, they are particularly vulnerable to impact forces that can partially or completely collapse the stent and possibly block fluid flow in the vessel. Under certain conditions, muscle contractions may even cause the stent to partially or totally collapse. Since balloon expandable stents are plastically deformed, once collapsed or crushed, they remain so, possibly blocking or occluding the vessel. These balloon expandable stents, therefore, could possibly pose an undesirable condition to the patient.

Such important applications as mentioned above have prompted stent designers to use superelastic or shape memory alloys in their stents to exploit the self-expanding and elastic properties of these materials. Typically, the superelastic or shape memory alloy of choice is nickel-titanium. Nickel-titanium alloy, commonly referred to as Nitinol, an acronym for Nickel-Titanium Naval Ordinance Laboratory, where it was initially developed, is frequently chosen for use in self-expanding stents and other medical devices due to its highly elastic behavior and resiliency. As a result, a nickel-titanium stent does not deform plastically when deployed, and remains highly resilient inside the body lumen. Because of this resilience, the self-expanding nickel-titanium stent can encounter a deforming impact, yet will return to its initial shape. Therefore, the chance of a permanent collapse of the self-expanding stent due to an impact force is minimized. An example of such shape memory alloy stents is disclosed in, for example, European Patent Application Publication No. EP0873734A2, entitled "Shape Memory Alloy Stent."

Near equi-atomic binary nickel-titanium alloys are known to exhibit "pseudoelastic" behavior when given certain cold working processes or cold working and heat treatment processes following hot working. Generally speaking, "pseudoelasticity" is the capacity of the nickel-titanium alloy to undergo large elastic strains on the order of 8 percent or more when loaded and to substantially fully recover all strain upon removal of the load. Substantially full recovery is typically understood to be less than 0.5 percent unrecovered strain, also known as permanent set or amnesia.

Pseudoelasticity can be further divided into two subcategories: "linear" pseudoelasticity and "non-linear" pseudoelasticity. "Non-linear" pseudoelasticity is sometimes used by those in the industry synonymously with "superelasticity."

Linear pseudoelasticity results from cold working only. Non-linear pseudoelasticity results from cold working and subsequent heat treatment. Non-linear pseudoelasticity, in its idealized state, exhibits a relatively flat loading plateau in which a large amount of recoverable strain is possible with very little increase in stress. This flat plateau can be seen in the stress-strain hysteresis curve of the alloy. Linear pseudoelasticity exhibits no such flat plateau. Non-linear pseudoelasticity is known to occur due to a reversible phase transformation from austenite to martensite, the latter more precisely called "stress-induced martensite" (SIM). Linear pseudoelasticity has no such phase transformation associated with it. Further discussions of linear pseudoelasticity can be found in, for example, T. W. Duerig, et al., "Linear Superelasticity in Cold-Worked Ni—Ti," *Engineering Aspects of Shape Memory Alloys*, pp. 414–19 (1990).

Because of the useful nature of the nickel-titanium alloy, some have attempted to change its properties to solve different design needs. For example, U.S. Pat. No. 6,106,642 to DiCarlo et al. discloses annealing Nitinol to achieve improved ductility and other mechanical properties. U.S. Pat. No. 5,876,434 to Flomenblit et al. teaches annealing and deforming Nitinol alloy to obtain different stress-strain relationships.

Binary nickel-titanium alloys have been used in the medical field. Some medical device related applications exploit the non-linear pseudoelastic capabilities of Nitinol. Examples include: U.S. Pat. Nos. 4,665,906; 5,067,957; 5,190,546; and 5,597,378 to Jervis; and U.S. Pat. Nos. 5,509,923; 5,486,183; 5,632,746; 5,720,754; and 6,004,629 to Middleman, et al.

Yet another application of nickel-titanium alloys is in an embolic protection or filtering device. Such embolic filtering devices and systems are particularly useful when performing balloon angioplasty, stenting procedures, laser angioplasty, or atherectomy in critical vessels, particularly in vessels such as the carotid arteries, where the release of embolic debris into the bloodstream can occlude the flow of oxygenated blood to the brain or other vital organs. Such an occlusion can cause devastating consequences to the patient. While the embolic protection devices and systems are particularly useful in carotid procedures, they are equally useful in conjunction with any vascular interventional procedure in which there is an embolic risk.

What has been needed and heretofore unavailable in the prior art is a medical device that exploits the benefits of linear pseudoelastic Nitinol. With the use of linear pseudoelastic Nitinol, the mechanical strength of the device is substantially greater per unit strain than a comparable device made of superelastic Nitinol. Furthermore, smaller component parts such as struts can be used because of the greater storage of energy available in a linear pseudoelastic Nitinol device.

SUMMARY OF THE INVENTION

The present invention is generally directed to cold worked nickel-titanium alloys and nickel-titanium clad alloys (nickel-titanium alloys clad with a layer of another metal) that have been deep drawn in a cold working process that produces linear pseudoelastic behavior in the alloy. The processed material may exhibit pseudoelastic behavior without a phase transformation or onset of stress-induced martensite as applied to a medical device.

In one aspect, the present invention is directed to a medical device for use in a body lumen comprising a structural element made from a cold formed nickel-titanium alloy which has been processed by plastically deforming a sheet-type product into a desired shape. Such processes may include deep drawing, pad forming, hydrodynamic forming or similar processing fundamentals commonly used in the metal forming industry. The nickel-titanium alloy remains in a martensitic phase when the structural element is stressed into a first shape and also when the stress to the structural element is relieved to assume a second shape. A sheath which at least partially envelopes the structural element in its first shape may be used to maintain a restraining force on the structural element. The sheath may be used to transport the medical device to a targeted location in the patient's anatomy, to deploy the medical device, and/or to retrieve the medical device at the end of the procedure.

The raw Nitinol for use in the present invention has been cold formed and is further cold worked to set the desired expanded shape through deep drawing processes. The deep drawing process can be accomplished, for example, by processing a sheet of Nitinol, referred to as a blank, in a press operation that utilizes a moveable punch or mandrel and a die to stamp the blank into a particular shaped element. The structural element, can be formed into a second desired shape by etching, lasing or mechanically cutting the structural element. The structural element can be further processed, through similar cutting or shaping operations, until it is formed into a final geometry to achieve the desired medical device or component of a composite medical device. Furthermore, the cold forming and cold working from the deep drawing procedure could occur below the recrystallization temperature of the Nitinol alloy.

During its operation, the linear pseudoelastic Nitinol medical device can be stressed without developing stress-induced martensite in the alloy. Consistent with this behavior, an idealized stress-strain curve of the linear pseudoelastic Nitinol does not contain any flat stress plateaus. Furthermore, despite application of stress, the Nitinol alloy does not undergo a phase transformation from austenite to martensite or vice versa.

The present invention produces a medical device which can have greater mechanical strength at any given strain as compared to a device made of a standard superelastic Nitinol. The stress-strain curve of the present invention may also possess more energy storage capacity. As a result, for a given desired performance requirement, the present invention linear pseudoelastic Nitinol device allows for smaller struts and consequently a lower profile useful in crossing narrow lesions.

Another advantage is that because the present invention uses linear pseudoelastic Nitinol, the underlying alloy can be selected from a broader range of available materials yet still maintain consistent, mechanical properties. In other words, there is less sensitivity to material variations and processing vagaries as compared to superelastic Nitinol. In addition, since the linear pseudoelastic Nitinol has no transformation from martensite to austenite or vice versa, there is less of an influence by temperature-related effects. As a result, a medical device, such as a stent, could be cold worked via the deep drawing process or similar cold forming processing, to assume a particular shape and may be ideally suited to accept drugs and coatings which may otherwise be temperature sensitive. Additional cold forming processing includes, but is not limited to, pad forming, hydrodynamic forming, stamping and other similar processing fundamentals commonly used in the metal forming industry. Further, such a medical device could be elastically compressed into a delivery sheath at room temperature, rather than at a lower temperature normally needed for processed Nitinol, in order to place the medical device into its compressed delivery position.

There are many specific applications for the present invention including vena cava filters, septal plugs, vascular grafts, just to name a few. One specific application of the present invention is a filtering device and system for capturing embolic debris in a blood vessel created during the performance of a therapeutic interventional procedure, such as a balloon angioplasty or stenting procedure, in order to prevent the embolic debris from blocking blood vessels downstream from the interventional site. Another specific application of the present invention is a stent, including an ostium stent, which can be formed with a flange that is positioned at the ostium of a body vessel to prevent the stent from displacement once implanted in the body vessel.

In another aspect of the present invention, it is no longer necessary to fabricate the structural element forming the medical device from, as an example, a small tubing that is then heat treated to an expanded state. Rather, the structural element can start out as a large diameter tubing and assembled inward to the desired geometry to create the structure of the medical device. The specific medical geometry shape can be formed from large tubing and compressed to a smaller size for delivery to accomplish the same expanded state without need of heat treatment to the nickel-titanium material.

In another aspect of the present invention, the nickel-titanium alloy can be clad with one or more additional layers of material, such as a thin layer of gold, platinum, or palladium, to increase the radiopacity of the nickel-titanium alloy. While nickel-titanium alloy is certainly beneficial for use in medical devices, one of its shortcomings is it's has low visibility under fluouroscopic examination. A material, such as biocompatible metal, however, can be clad over the surface of the nickel-titanium alloy to increase the radiopacity on the fluoroscoping. The nickel-titanium clad material can then be processed as described above to create a medical device or component of a composite medical device having a desired geometry. Methods for cladding or depositing one or more layers of materials onto nickel-titanium, such as electro plating, are known in the art.

In another aspect of the present invention, the material can first be annealed at a particular temperature then shaped by the deep drawing process to create a particular shape which can then be further processed (through the use of a laser or other processing means) to obtain the desired medical device geometry. Upon further processing, the particular geometry of the medical device can take on many different forms and shapes and could have many different applications in the medical field. However, the annealing process may cause this particular processed material to behave more like non-linear pseudoelastic Nitinol.

Other features and advantages of the present invention will become more apparent from the following detailed description of the invention when taken in conjunction with the accompanying exemplary drawings.

BRIEF DESCRIPTION OF THE DRAWINGS

FIG. 10 is a perspective view of the expandable cage of FIG. 9 as it is mounted onto a guide wire and attached to a filtering member to form an embolic filtering device.

FIG. 11 is a perspective view of the embolic filtering device of FIG. 10 with the filtering member removed to better show the expandable cage.

DETAILED DESCRIPTION OF THE PREFERRED EMBODIMENTS

The present invention is generally directed to a process by which nickel-titanium alloys and nickel-titanium clad with a radiopaque material can be initially cold worked by any of the multiple methods to cold work material, such as a deep drawing operation that creates a specially-shaped element that can be farther processed and shaped to assume a particular medical geometry. The cold worked nickel-titanium material may have linear pseudoelastic behavior without a phase transformation or onset of stress-induced martensite as applied to a medical device having a structural element deployed from a restraining sheath. Although the present invention is applicable to, and contemplates numerous medical devices, for the sake of illustration, the following detail description focuses on exemplary embodiments formed as a filtering device for capturing embolic debris and a self-expanding stent. However, it is recognized that the present invention is not limited to such applications and rather may be used in various other medical devices (e.g., guide wires, endovascular grafts, vena cava filters, septal plugs, etc.) where the same principles are applicable. It should be appreciated that components which form part of a composite medical device can be made as well in accordance with the present invention.

Figures 1, 2:
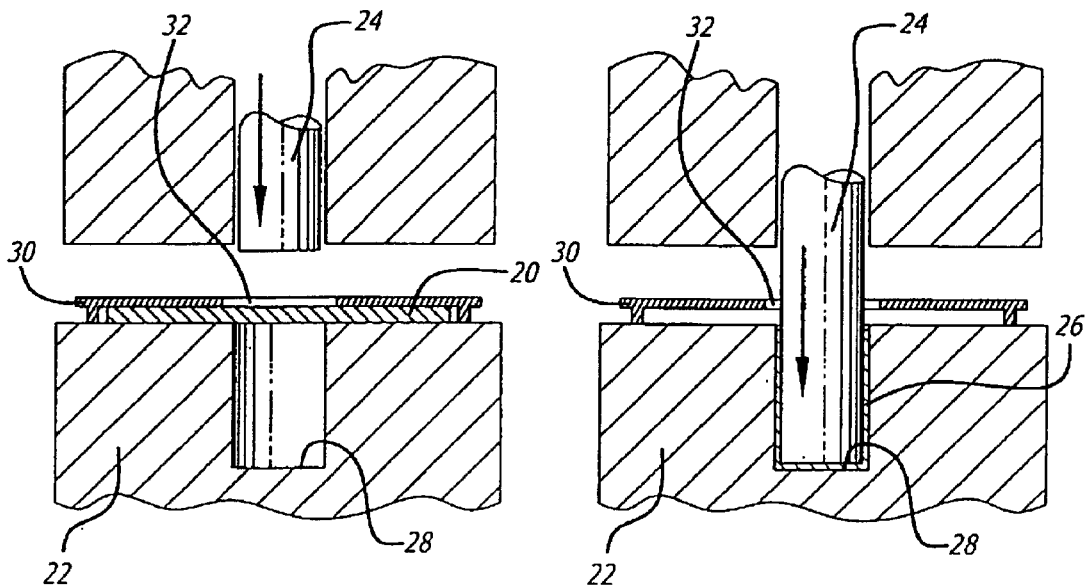
FIG. 1 is a schematic representation of a sheet of nickel-titanium alloy or nickel-titanium clad alloy placed on a die and ready to be deep drawn by a cylindrical punch or mandrel.
FIG. 2 is a schematic representation, similar to FIG. 1, wherein the sheet of nickel-titanium alloy or nickel-titanium clad alloy is deep drawn by the cylindrical punch to form a tubing which can be further processed and shaped into a medical device.

Turning now to the drawings, in which like reference numerals represent like or corresponding elements, FIGS. 1 and 2 illustrate a schematic representation of a deep drawing process which can be used to process the nickel-titanium alloy or nickel-titanium alloy clad material in accordance with the present invention. As can be seen in FIGS. 1 and 2, a sheet 20 of nickel-titanium alloy, commonly referred to as a blank, is shown placed over a die 22 and ready for the deep drawing operation which is performed by a punch 24 or mandrel that exerts a downward force on the sheet 20. The action of the punch 24 on the sheet 20 creates a structural element 26, such as the element shown in FIG. 5. The punch 24 or mandrel is shown substantially cylindrically-shaped although any number of different size and shaped punches could be utilized. The punch 24 can be actuated pneumatically or hydraulically, or by any other means, to cause the punch to plastically deform the sheet 20 of nickel-titanium alloy into the desired configuration. The die 22 has a cavity 28 which also helps to form the composite shape of the deep drawn structural element 26. It should be appreciated that FIGS. 1–4 merely depict schematically representative embodiments of a punch and die apparatus and that any one of a number of deep drawing machinery could be utilized in accordance with the present invention to create the structural element 26.

Referring still to FIGS. 1 and 2, the sheet 20 of the nickel-titanium alloy remains in place on the die 22 by a hold down plate 30 which has an opening 32 through which the punch 24 extends. This hold down plate 30, as its name applies, is utilized to help maintain the sheet 20 in place as the punch 24 extends downwardly to deep draw the sheet 20 into the cavity 28. One skilled in the art will recognize that other means for holding the material in place could be utilized as well.

Figures 3, 4:
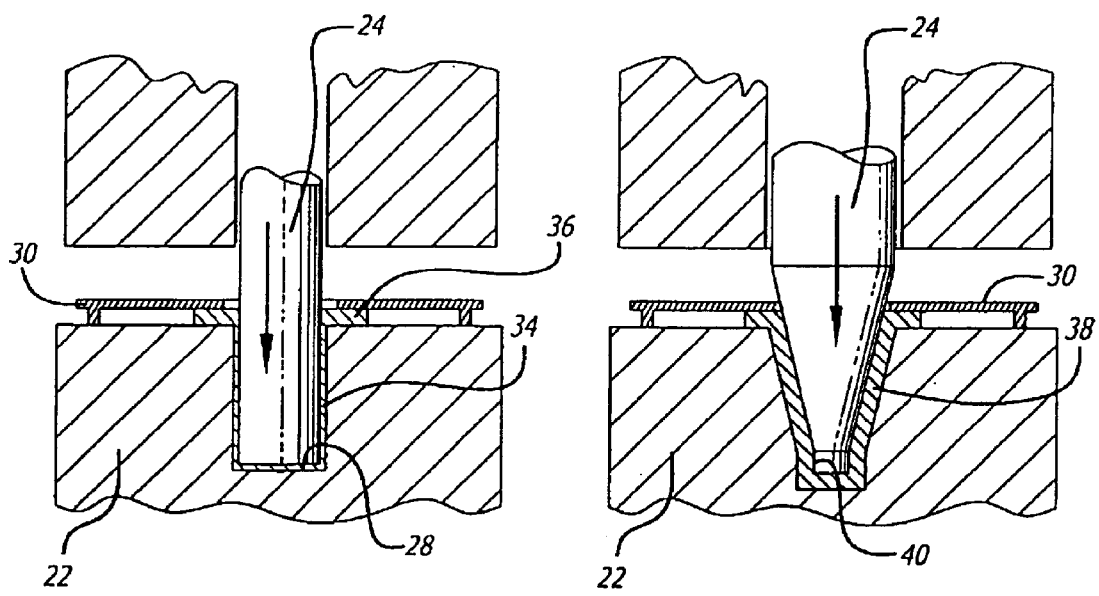
FIG. 3 is a schematic representation, similar to FIG. 2, wherein the sheet of nickel-titanium alloy or nickel-titanium clad alloy is deep drawn by the cylindrical punch to form a tubing with a flange which can be further processed and shaped into a medical device.
FIG. 4 is a schematic representation, similar to FIG. 2, wherein the sheet of nickel-titanium alloy or nickel-titanium clad alloy is deep drawn by a specially-shaped punch in a specially-shaped die to form a particular sized element which can be further processed and shaped into a medical device.
Figure 5:
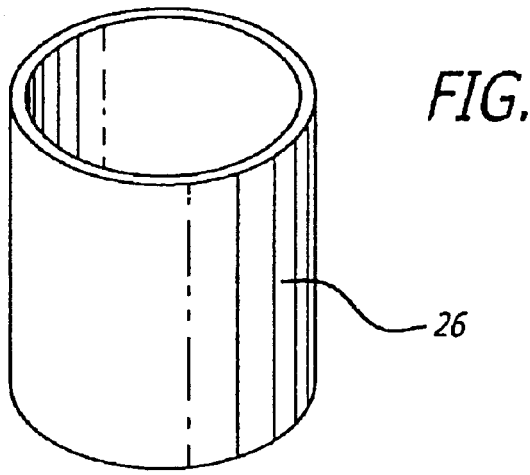
FIG. 5 is a representative cylindrically-shaped tubing which can be formed by the deep drawing process depicted in FIGS. 1 and 2.
Figure 6:
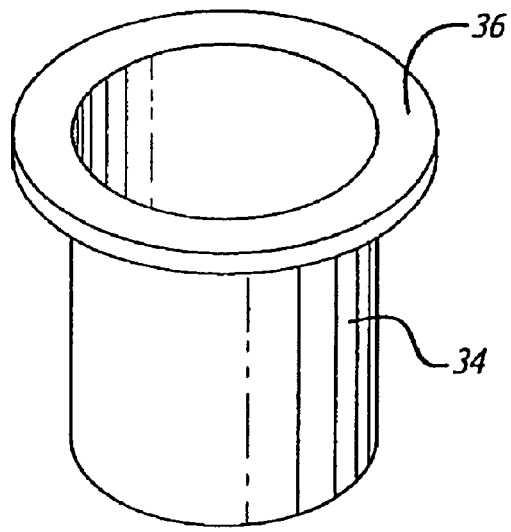
FIG. 6 is a representative specially-shaped element which can be formed by the deep drawing process depicted in FIG. 3.

Referring now to FIG. 3, a similar schematic representation of a punch 24 which forms the deep drawn structural element 34, shown in FIG. 6, is illustrated. As can be seen in FIG. 6, the deep drawn structural element 34 has a somewhat different shape than the deep drawn structural element 26 created in the process depicted in FIGS. 1 and 2. This particular deep drawn structural element 34 includes a flanged region 36 formed to create a particular shape that can be further processed into, for example, the ostial stent shown in FIGS. 12 and 13. The deep drawn structural element 26 of FIG. 5 is cylindrically-shaped and cup-like and can be farther processed to create the medical device of interest, for example, an expandable cage for an embolic filtering device, as is depicted in FIGS. 8 and 9.

Figure 7:
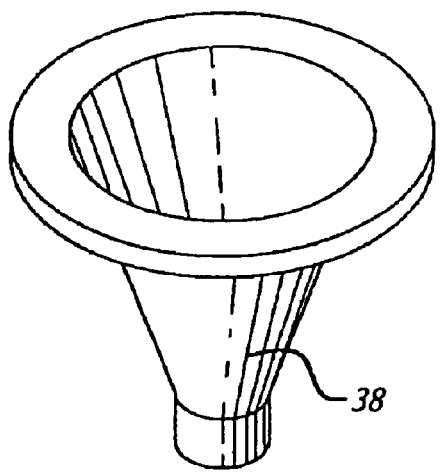
FIG. 7 is a representative specially-shaped element which can be formed by the deep drawing process depicted in FIG. 4.

Referring now to FIG. 4, an alternative punch and die assembly is shown which again is depicted for purposes of illustrating the various types of punches and dies that can be utilized in accordance with the present invention to create the desired shape of the structural element. As can be seen in FIG. 4, the punch 24 has a tapered shape to form a deep drawn structural element 38, depicted in FIG. 7. Accordingly, the die 22 includes a cavity 40 specifically shaped to create the configuration of this particular structural element 38. Again, this figure represents one of many different apparatus that can be utilized in accordance with the present invention to create the deep drawn element which can be later processed into the desired medical device. It also should be appreciated that a punch and die or similar apparatus could be utilized to cut or further shape the structural element into a secondary shape which could be formed into the finished device. Alternatively, further deep drawing processing may be implemented until the structural element is worked into the desired structure. Processing operations could utilize cutting dies and punches well-known in the art.

Figure 8:
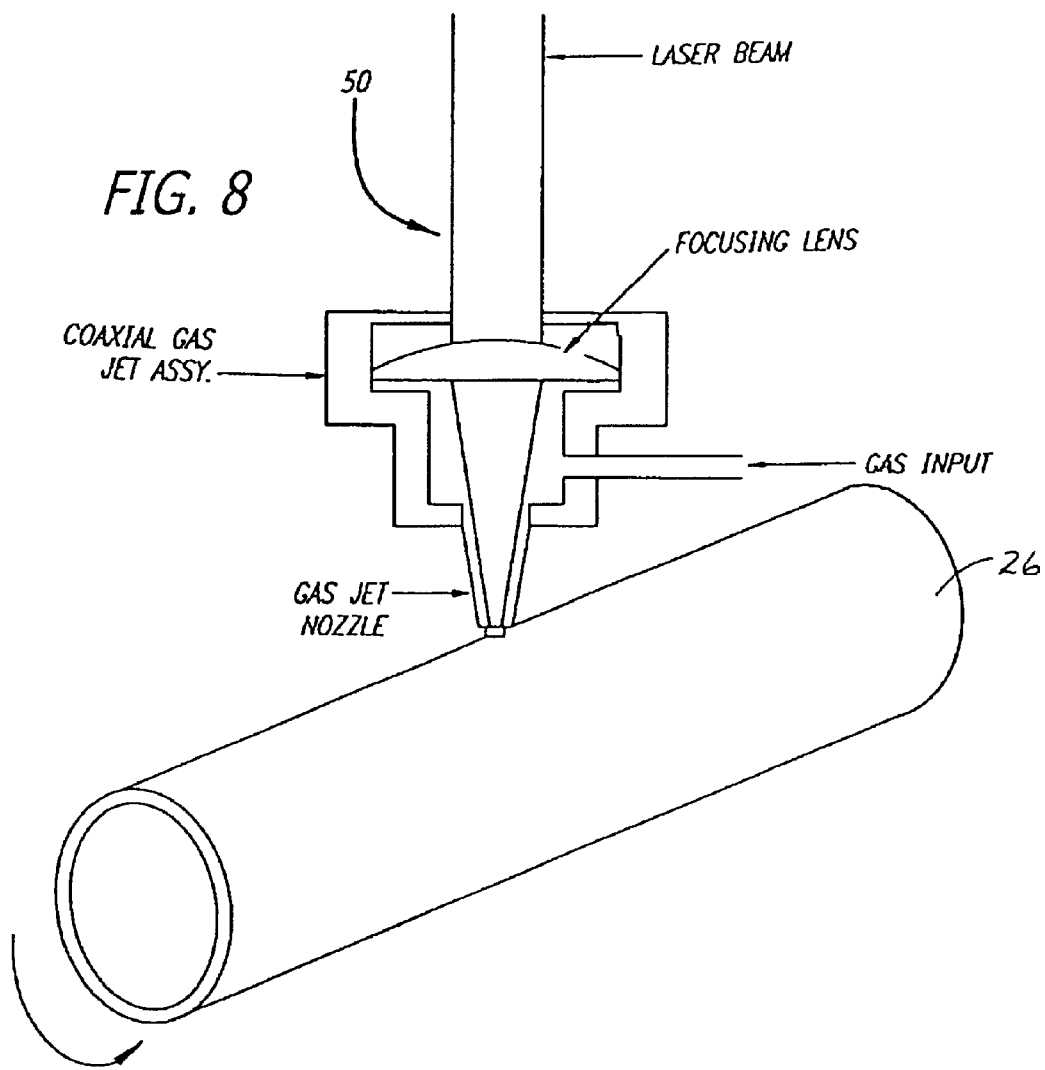
FIG. 8 is a perspective view of a cylindrically-shaped tubing, as shown in FIG. 5, and a laser cutting apparatus which can selectively remove material from the tubing to form a specifically-shaped medical device.
Figure 9:
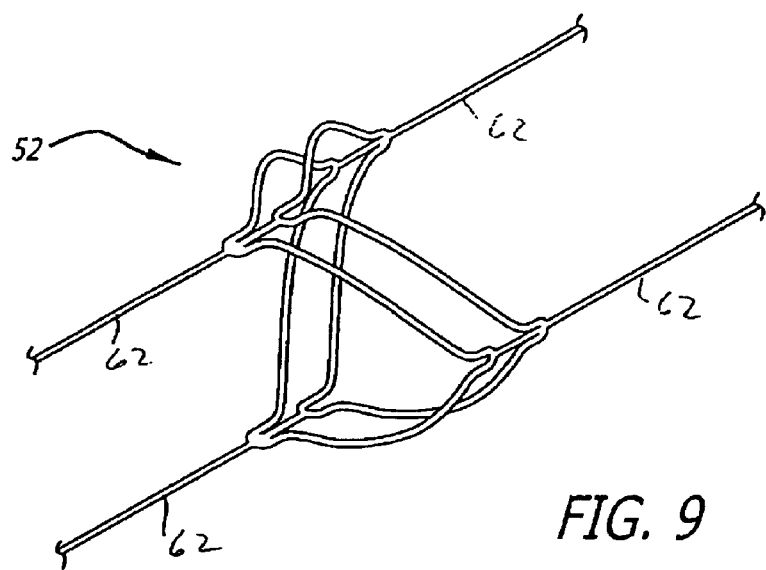
FIG. 9 is a perspective view of the cylindrically-shaped tubing of FIG. 8 after the laser cutting apparatus selectively removes material to form an expandable cage that can be used in conjunction with an embolic filtering device.

Referring now to FIGS. 8–11, one particular form of a medical device made in accordance with the present invention and the process for manufacturing the device are shown. Referring initially to FIG. 8, the structural element 26, which already has been deep drawn, for example, in the operation depicted in FIGS. 1 and 2, is shown being laser cut into a final configuration to produce a desired medical device geometry. As can be seen in FIG. 8, the structural element 26 is being laser cut by a laser assembly 50 schematically depicted in FIG. 8. In this manner, the laser apparatus 50 selectively removes material from the structural element 26 to create the desired medical device geometry, as is shown in FIG. 9. The structural element 26 can be mounted onto a mandrel (not shown) which is rotatable to assist the laser cutting operation. It should be appreciated to those skilled in the art that the structural element 26 could also be formed into the desired configuration by chemical etching, mechanical cutting processes, and other techniques known in the art.

Referring now to FIG. 9, it can be seen that the laser apparatus has selectively removed material from the structural element 26 to create an expandable embolic cage 52 used to form the embolic filtering device 54 as shown in FIGS. 10 and 11. It should be appreciated that this is just one example of a medical device which can be formed from a structural element formed in accordance with the present invention.

This embolic filtering device 54 is designed to capture embolic debris which may be created and released into a body vessel during, for example, an interventional procedure. The embolic filtering device 54 has an expandable filter assembly 55 which includes the expandable cage 52 and a filter element 56 attached thereto. In this particular embodiment, the expandable filter assembly 55 is rotatably mounted on the distal end of an elongated (solid or hollow) cylindrical tubular shaft, such as a guide wire 58. The expandable filter assembly 55 could also be attached directly onto the guide wire, so as not to rotate independently of the guide wire. The guide wire has a proximal end (not shown) which would extend outside the patient and is manipulated by the physician to deliver the filter assembly into the target area in the patient's vasculature. A restraining or delivery sheath (not shown) would extend coaxially along the guide wire in order to maintain the expandable filter assembly 55 in its collapsed or unexpanded position until it is ready to be deployed within the patient's vasculature. The expandable filter assembly 55 can be deployed by the physician by simply retracting the restraining sheath proximally to expose the expandable filter assembly. Once the restraining sheath is retracted, the expandable cage 52 immediately begins to expand within the body vessel, causing the filter element 56 to expand as well.

The embolic filtering device 54 is shown with an obturator 60 affixed to the distal end of the filter assembly 55 to prevent possible "snowplowing" of the embolic filtering device as it is being delivered through the vasculature. The obturator can be placed adjacent to the end of the delivery sheath to create a streamline profile with the sheath. The obturator can be made from a soft polymeric material and has a smooth surface to help the embolic filtering device travel through the vasculature and cross lesions while preventing the distal end of the restraining sheath from otherwise "digging" or "snowplowing" into the wall of the body vessel.

The expandable cage includes self-expanding struts 62 which, upon release from the restraining sheath, expand the filter element into a deployed position within the artery or other body vessel. Embolic particles created during the interventional procedure and released into the bloodstream are captured within the deployed filter element. The filter includes perfusion openings, or other suitable perfusion means, for allowing blood flow through the filter. The filter element will capture embolic particles which are larger than the perfusion openings while allowing some blood to perfuse downstream to vital organs.

Referring specifically to FIG. 9, the expandable cage 42 is shown as it appears after it has been cut from a tubular member. As can be seen, the free ends of the proximal and distal struts 62 are initially spread apart after being formed from the tubular shaped structural element. The free ends of the struts 62 can be attached to a collar 64, such as is shown in FIGS. 10 and 11, to allow the expandable cage 42 to be mounted to the guide wire. The free ends of the proximal and distal struts can be fastened to the collar using known bonding techniques, including, braising, soldering, welding, as well as adhesive bonding. A pair of circumferential members 63 and 65 form the expandable cage 52 and are self-expanding to help deploy the filter element 56.

The expandable cage 42 of the present invention is shown rotatably mounted to the distal end of the guide wire to allow the entire filter assembly to remain stationary once deployed in the body vessel. This feature prevents the filtering assembly from rotating against the wall of the body vessel in the event that the proximal end of the guide wire should be rotated by the physician during use. As a result, the possibility that the deployed filter assembly could be rotated to cause trauma to the wall of the vessel is minimized. Referring again to FIGS. 10 and 11, a pair of stop fittings 66 and 68 are placed on the guide wire to maintain the collar 64, and hence the proximal end of the expandable cage 42, rotatably fixed to the guide wire. These stop fittings 66 and 68 allow the expandable cage 42 to spin on the guide wire while restricting the longitudinal movement of the cage on the guide wire. This particular mechanism is just one way in which the expandable cage can be mounted to the guide wire. Alternatively, the expandable cage can be attached directly onto the guide wire so as not to rotate independently.

Figure 12:
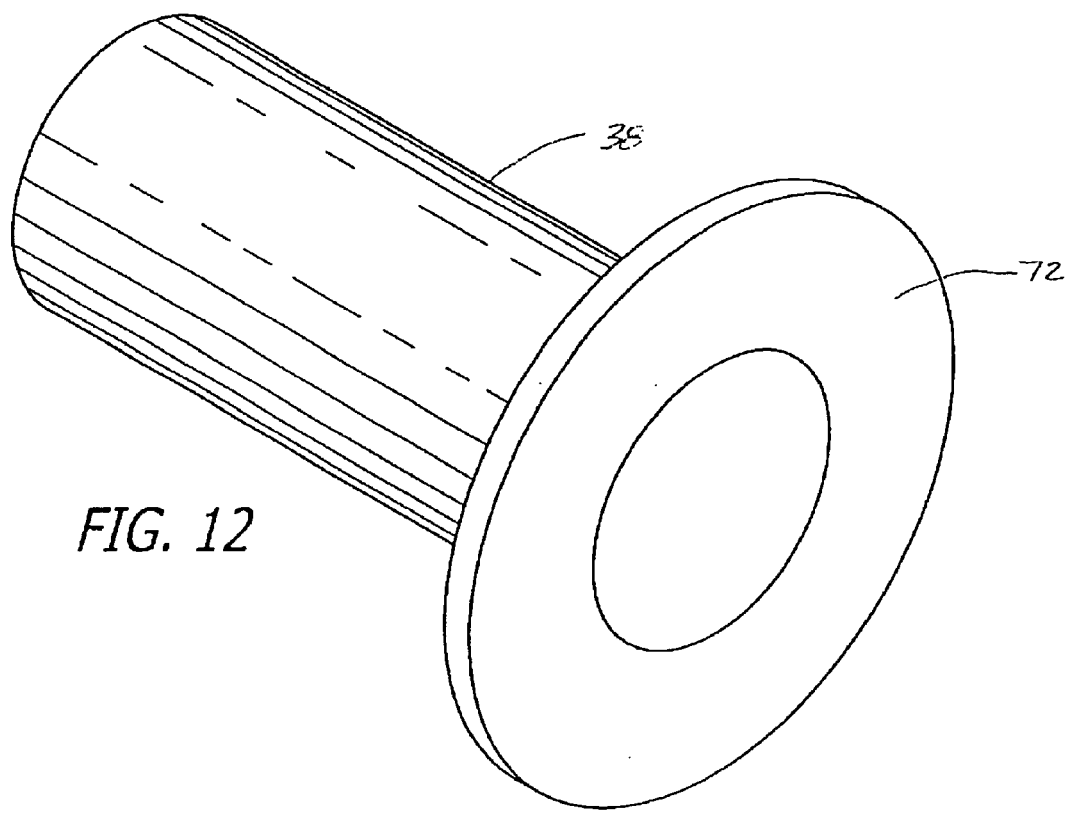
FIG. 12 is a perspective view of the deep-drawn element of FIG. 6 which can be laser cut to form a specifically-shaped medical device.
Figure 13:
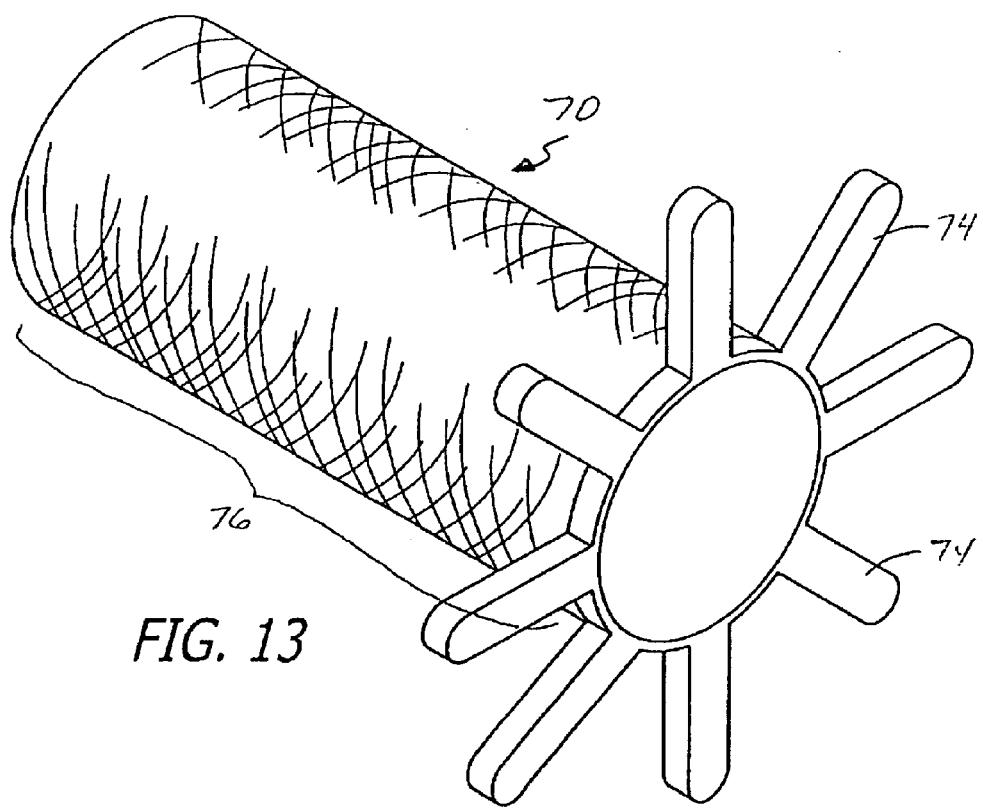
FIG. 13 is a perspective view of the deep drawn element of FIG. 12 after being laser cut into a specifically-shaped medical device, namely, a self-expanding stent.

Referring now to FIGS. 12 and 13, a particular structural element 36 which is processed into a medical device is shown. The structural element 36 can be laser cut into a specific geometry, such as the self-expanding, ostial stent 70 shown in FIG. 13. A flange 72 formed on the structural element 36 allows the creation of the "pedals" 74 which form a flared portion of the stent 70. The ostial stent 70 can be placed in a vascular location, for example, a bifurcated vessel, such that the main body 76 of the stent 70 is placed in the diseased portion of the bifurcated vessel with the flanged portion or pedals 74 substantially conforming to the vessel wall at the ostium of the diseased vessel. The construction and particular use of the ostial stent depicted here is described in greater detail in U.S. Pat. No, 5,607,444, which is assigned to Advanced Cardiovascular Systems, Inc.

The structural element 36 of FIG. 12 can be laser cut Nitinol tubing that can be further cold formed and specifically cold worked with no heat treatment such that it remains in a fully martensitic state. The cold working proceeds only at temperatures below the recrystallization temperature of the Nitinol alloy. Next, the lase-cut Nitinol tubing can be cold worked to its desired expanded size. The desired expanded size is thus imparted or set into the laser cut tube. In one particular embodiment of the present invention, the ingot transformational temperature of the nickel-titanium alloy can be set above 37 degrees Celsius.

Importantly, the laser-cut Nitinol tubing is not heat treated to prevent generation of any loading or unloading plateaus in the stress-strain curve. In an alternative embodiment, the Nitinol tubing may undergo heat treating for only very limited durations at low temperatures. The present invention recognizes that a significant difference between linear pseudoelasticity and non-linear pseudoelasticity is the absence or presence, respectively, of stress-induced martensite. It also recognizes that in order to set a particular shape in Nitinol, the Nitinol must be heat treated at a relatively high temperature for a short period of time. Under normal circumstances, this material would then exhibit non-linear pseudoelasticity and therefore would undergo a reversible phase transformation from austenite to martensite. When setting a shape under standard conditions, for example, 550 degrees C. for 5 minutes, the Nitinol exhibits essentially no springback; that is, its unconstrained shape after heat treatment is nearly identical to its constrained shape during heat treatment. The Nitinol does not spring back to its original shape prior to heat treatment. At the other extreme, linear pseudoelastic Nitinol with no heat treatment has 100 percent springback and always returns to its original, cold worked shape.

Springback is a continuous function between no heat treatment (100 percent springback) and ideal shape setting heat treatment (approximately zero percent springback). From an engineering perspective for design of Nitinol based pseudoelastic devices, less springback is more favorable than more springback. However, in some circumstances, linear pseudoelasticity may be preferable to non-linear pseudoelasticity. Therefore, the present invention, in addition to contemplating cold-worked only Nitinol, addresses that regime of heat treatment temperatures and times within which springback is adequately minimized to successfully impart a desired shape to the Nitinol structure and within which the Nitinol does not develop a stable and reversible martensitic phase.

In one particular embodiment of the present invention, to achieve the linear pseudoelastic behavior, the binary nickel-titanium tubing has approximately 55.8 atomic percent nickel. The tubing must contain a minimum of approximately 38 percent cold working when measured by the reduction in cross-sectional area, and there is not to be any heat treatment following final cold reduction. As to the alternative embodiment, the present invention contemplates accumulated heat treatment of the tubing of up to 300 degrees C. for up to 5 minutes. Under ideal conditions, these process parameters should adequately ensure that the Nitinol remains martensitic without a phase change under stress.

Figure 14:
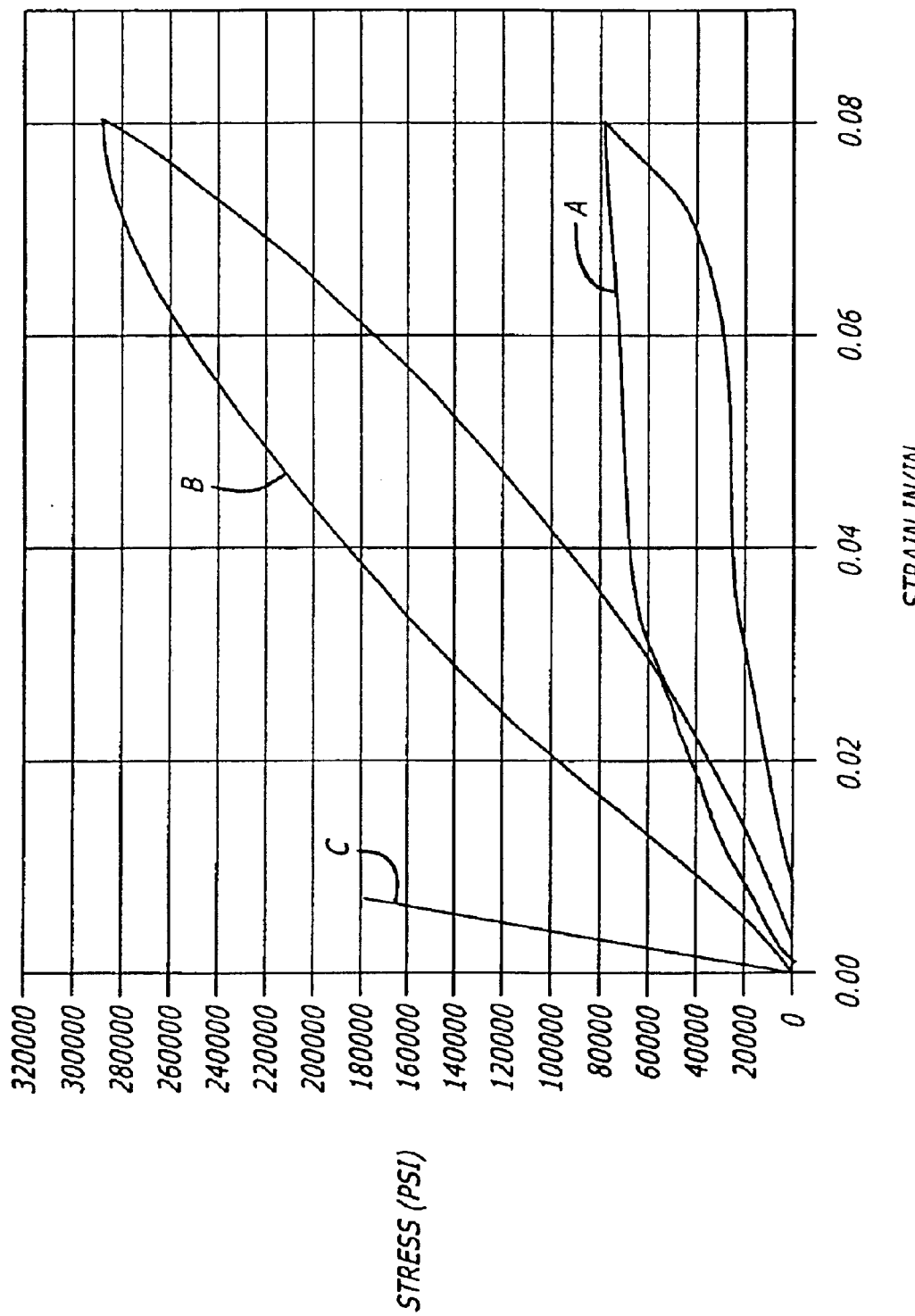
FIG. 14 is a set of stress-strain curves for conventional 316L stainless steel, linear pseudoelastic Nitinol, and non-linear pseudoelastic Nitinol.

To illustrate the metallurgical aspects of cold worked nickel-titanium alloys, FIG. 14 contains the elastic component of three idealized stress-strain curves for 316L stainless steel, linear pseudoelastic Nitinol, and non-linear pseudoelastic Nitinol. In a preferred embodiment, the expandable strut assembly 14 of the present invention is formed partially or completely of alloys such as the linear pseudoelastic Nitinol shown in FIG. 14.

In FIG. 14, in an idealized curve A for a non-linear pseudoelastic Nitinol, the relationship is plotted on x-y axes, with the x axis representing strain and the y axis representing stress. The x and y axes are labeled in units of stress from zero to 320 ksi and strain from 0 to 9 percent, respectively.

In curve A, when stress is applied to a specimen of a metal such as Nitinol exhibiting non-linear pseudoelastic characteristics at a temperature at or above that which the transformation of the martensitic phase to the austenitic phase is complete, the specimen deforms elastically until it reaches a particular stress level where the alloy then undergoes a stress-induced phase transformation from the austenitic phase to the martensitic phase (i.e., the stress-induced martensite phase). As the phase transformation progresses, the alloy undergoes significant increases in strain with little or no corresponding increases in stress. On curve A this is represented by upper, nearly flat stress plateau at approximately 70 to 80 ksi. The strain increases while the stress remains essentially constant until the transformation of the austenitic phase to the martensitic phase is complete. Thereafter, further increase in stress is necessary to cause further deformation. The martensitic metal first yields elastically upon the application of additional stress and then plastically with permanent residual deformation (not shown).

If the load on the specimen is removed before any permanent deformation has occurred, the martensite specimen elastically recovers and transforms back to the austenitic phase. The reduction in stress first causes a decrease in strain. As stress reduction reaches the level at which the martensitic phase transforms back into the austenitic phase, the stress level in the specimen remains essentially constant (but less than the constant stress level at which the austenitic crystalline structure transforms to the martensitic crystalline structure until the transformation back to the austenitic phase is complete); i.e., there is significant recovery in strain with only negligible corresponding stress reduction. This is represented in curve A by the lower stress plateau at about 20 ksi.

After the transformation back to austenite is complete, further stress reduction results in elastic strain reduction. This ability to incur significant strain at relatively constant stress upon the application of a load and to recover from the deformation upon the removal of the load is commonly referred to as non-linear pseudoelasticity (or superelasticity).

FIG. 14 also has a curve B representing the idealized behavior of linear pseudoelastic Nitinol as utilized in the present invention. Curve B does not contain any flat plateau stresses found in curve A. This stands to reason since the Nitinol of curve B remains in the martensitic phase throughout and does not undergo any phase change. The same tension and release of stress cycle to generate curve A is used to generate curve B. To that end, curve B shows that increasing stress begets a proportional increase in reversible strain, and a release of stress begets a proportional decrease in strain. The areas bounded by curves A and B represent the hysteresis in the Nitinol.

As apparent from comparing curve B to curve A in FIG. 14, with the use of linear pseudoelastic Nitinol, the mechanical strength of the present invention medical device is substantially greater per unit strain than a comparable device made of superelastic Nitinol. Consequently, a major benefit is that smaller component parts such as struts can be used because of the greater storage of energy available in a linear pseudoelastic Nitinol device. A small profile is one critical factor for crossing narrow lesions or for accessing remote and tortuous arteries.

FIG. 14 includes curve C which is the elastic behavior of a standard 316L stainless steel. Stress is incrementally applied to the steel and, just prior to the metal deforming plastically, decrementally released. It is provided here simply for comparison to curves A and B.

As mentioned above, the present invention medical device uses preferably a binary nickel-titanium alloy. In an alternative embodiment, however, the nickel-titanium may be clad with another element such as palladium, platinum, chromium, iron, cobalt, vanadium, manganese, boron, copper, aluminum, tungsten, gold, tantalum, or zirconium. The nickel-titanium alloy can also be a ternary alloy, in which a third element is added to from the nickel-titanium based alloy. In such a case, the additional element is not clad or deposited on the outer surface of the nickel-titanium alloy, but rather, combines with the nickel-titanium to form a ternary alloy. For example, the nickel-titanium alloy could further include a ternary element selected from the group of chemical elements consisting of iridium, platinum, gold, rhenium, tungsten, palladium, rhodium, tantalum, silver, ruthenium or hafnium.

Generally, the structural element can be placed in a rotatable collet fixture of a machine-controlled apparatus for positioning the tubing relative to a laser. According to machine-encoded instructions, the structural element is then rotated and moved longitudinally relative to the laser which is also machine-controlled. The laser selectively removes the material from the structural element by ablation and a pattern is cut into the structural element. The structural element is therefore cut into the discrete pattern of the finished medical device, such as a stent. The expandable cage can be laser cut much like a stent is laser cut. Details on how the tubing can be cut by a laser are found in U.S. Pat. No. 5,759,192 (Saunders), U.S. Pat. No. 5,780,807 (Saunders) and 6,131,266 (Saunders) which have been assigned to Advanced Cardiovascular Systems, Inc.

The process of cutting a pattern into the structural element generally is automated except for loading and unloading the length of the structural element. For example, a pattern can be cut in the structural element using a CNC-opposing collet fixture for axial rotation of the length of the structural element, in conjunction with CNC X/Y table to move the length of the structural element axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

While the present invention has been illustrated and described herein in terms of linear pseudoelastic Nitinol filter assembly of an embolic protection device and its delivery system and a self-expanding stent, it is apparent to those skilled in the art that the present invention be used in other instances. Other modifications and improvements may be made without departing from the scope of the present invention.

What is claimed is:

1. A medical device, comprising:
   a structural element having a particular medical device geometry formed from nickel-titanium alloy and being collapsible to be placed in a delivery position and self-expandable from the delivery position to a deployed position, where the nickel-titanium alloy has been processed in a deep drawing process which forms hollow-shaped structural element and cold works the nickel-titanium alloy so that it remains in a martensitic phase only regardless of stress that may be applied to the structural element to maintain the structural element in the delivery position, the hollow-shaped structural element being formed into the desired medical device geometry which includes a hollow structure.

2. The medical device of claim 1, wherein the structural element is laser cut to form the medical device geometry.

3. The medical device of claim 1, wherein the nickel titanium alloy is clad with a metallic element.

4. The medical device of claim 3, wherein the metallic element clad onto the nickel-titanium alloy is selected from the group consisting of palladium, platinum, chromium, iron, cobalt, vanadium, manganese, boron, copper, aluminum, tungsten, gold, tantalum and zirconium.

5. The medical device of claim 1, wherein the structural element has been heat treated and a hysteresis curve of the nickel-titanium alloy does not include a stress plateau.

6. The medical device of claim 1, wherein the structural element assumes a shape imparted by cold forming.

7. The medical device of claim 6, wherein the deep drawing occurs below the recrystallization temperature of the nickel-titanium alloy.

8. The medical device of claim 1, wherein the nickel-titanium alloy has an ingot transformation temperature which is set above 37 degrees C.

9. The medical device of claim 1, wherein the structural element forms a component of a composite medical device.

10. The medical device of claim 1, wherein the nickel-titanium alloy contains a third element.

11. The medical device of claim 10, wherein the third element is selected from a group consisting of iridium, platinum, gold, rhenium, tungsten, palladium, rhodium, tantalum, silver, ruthenium or hafnium.

12. A method for manufacturing a medical device for use in a body lumen, comprising:
   providing nickel-titanium stock;
   deep drawing the nickel-titanium alloy stock into a structure element having a hollow shape; and
   forming the structural element into a desired medical device geometry which includes a hollow structure, the structural element being capable of assuming a first position when a stress is applied to it and movable to a second position when the stress is removed.

13. The method for manufacturing a medical device of claim 12, wherein the deep drawing of the nickel-titanium alloy produces a material which remains in a martensitic phase regardless of stress that may be applied to the structural element.

14. The method for manufacturing a medical device of claim 12, wherein the deep drawing of the nickel-titanium stock is performed by a punch and die operation.

15. The method for manufacturing a medical device claim 12, wherein method includes low temperature heat treat of the nickel-titanium alloy.

16. A self-expanding medical device, comprising:
a structural element having a particular medical device geometry formed from a nickel-titanium alloy and being collapsible to be placed in a delivery position and self-expandable from the delivery position to a deployed position, wherein the nickel-titanium alloy has been processed in a deep drawing process which forms hollow-shaped structural element and cold works the nickel-titanium alloy and heat treated so that the alloy remains in a martensitic phase only regardless of stress that may be applied to the structural element to maintain the structural element in the delivery position, the hollow-shaped structural element being formed into the desired medical device geometry which includes a hollow structure.

17. The medical device of claim 16, wherein the structural element is laser cut to form the medical device geometry.

18. The medical device of claim 16, wherein the nickel-titanium alloy is clad with a metallic element.

19. The medical device of claim 16, wherein the structural element assumes a shape imparted by cold forming.

20. The medical device of claim 16, wherein the nickel-titanium alloy contains a third element.

* * * * *